(12) United States Patent
Mehta et al.

(10) Patent No.: US 8,287,848 B2
(45) Date of Patent: Oct. 16, 2012

(54) FORMULATIONS CONTAINING AN IONIC MINERAL-ION EXCHANGE RESIN COMPLEX AND USES THEREOF

(75) Inventors: Ketan Mehta, Cranbury, NJ (US); Yu-Hsing Tu, West Windsor, NJ (US); Mahendra Shah, Long Grove, IL (US)

(73) Assignee: Tris Pharma Inc, Monmouth Junction, NJ (US)

( * ) Notice: Subject to any disclaimer, the term of this patent is extended or adjusted under 35 U.S.C. 154(b) by 559 days.

(21) Appl. No.: 12/441,918

(22) PCT Filed: Sep. 27, 2007

(86) PCT No.: PCT/US2007/020844
§ 371 (c)(1), (2), (4) Date: Mar. 19, 2009

(87) PCT Pub. No.: WO2008/042218
PCT Pub. Date: Apr. 10, 2008

(65) Prior Publication Data
US 2009/0317488 A1   Dec. 24, 2009

Related U.S. Application Data

(60) Provisional application No. 60/827,974, filed on Oct. 3, 2006.

(51) Int. Cl.
  A61K 31/74   (2006.01)
  A61K 47/00   (2006.01)
  A61K 9/14    (2006.01)
  A61K 33/26   (2006.01)

(52) U.S. Cl. ........ 424/78.1; 424/646; 424/439; 424/489

(58) Field of Classification Search ............. 424/78.1, 424/646, 439, 489
See application file for complete search history.

(56) References Cited

U.S. PATENT DOCUMENTS

| | | | |
|---|---|---|---|
| 2,990,332 A | 6/1961 | Keating | |
| 3,027,303 A | 3/1962 | Wolcott | |
| 3,138,525 A | 6/1964 | Koff | |
| 3,499,960 A | 3/1970 | Macek | |
| 3,594,470 A | 7/1971 | Borodkin | |
| 3,947,572 A | 3/1976 | Borodkin | |
| 4,837,015 A * | 6/1989 | Olsen | 424/78.1 |
| 5,017,389 A * | 5/1991 | Green | 426/72 |
| 5,883,083 A * | 3/1999 | Harless | 514/78 |
| 6,579,544 B1 * | 6/2003 | Rosenberg et al. | 424/736 |
| 6,814,983 B2 * | 11/2004 | Giordano et al. | 424/630 |
| 8,062,667 B2 | 11/2011 | Mehta et al. | |
| 2005/0037065 A1 * | 2/2005 | Kirschner et al. | 424/456 |
| 2006/0286174 A1 | 12/2006 | Raman et al. | |
| 2007/0215511 A1 | 9/2007 | Mehta et al. | |
| 2010/0166858 A1 | 7/2010 | Mehta | |

FOREIGN PATENT DOCUMENTS

| | | |
|---|---|---|
| BE | 729827 | 3/1969 |
| DE | 2246037 | 4/1974 |
| GB | 2 218 333 A | 11/1989 |
| JP | 2108625 | 4/1990 |

OTHER PUBLICATIONS

Brugnara et al, Reticulocyte Hemoglobin content (CHr): Early indicator of Iron Deficiency and Response to Therapy, Blood, 83:3100-3101, (May 1994).
Citing Drug Facts and Comparisons, Ferrous Sulfate, updated (Nov. 2003), Taken from website: www.drugs.com.
Iost et al, Repleting Hemoglobin in Iron Deficiency Anemia in Young Children through Liquid Milk Fortification with Bioavailable Iron Amino Acid Chelate, Journal of the American College of Nutrition, vol. 17, No. 2, pp. 187-194, (Apr. 1998).
Navarrete-Guijosa et al, Lithium Adsorption by Acid and Sodium Amberlite, Journal of Colloid and Interface Science, (Aug. 2003).
Oshtrack et al, Analysis of the Iron State in Iron Containing Vitamins and Dietary Supplements by Mössbauer Spectroscopy, Analytica Chimica Acta, 506:155-160, (2004).
Pediatric Pharmacotherapy, A Monthly Newsletter for Health Care Professionals Children's Medical Center at the University of Virginia, vol. 2, No. 9, pp. 1-4, (Sep. 1996).
Pharmacy and Therapeutics Committee Medication Review, Oral Iron-Containing Products, pp. 1-7, (May 21, 2004).
Pineda et al, Effectiveness of Treatment of Iron-Deficiency Anemia in Infants and Young Children with Ferrous Bis-Glycinate Chelate, Nutrition, vol. 17, No. 5, (May 2001).
Pineda et al, Effectiveness of Iron Amino Acid Chelate on the Treatment of Iron Deficiency Anemia in Adolescents, Journal of Applied Nutrition, vol. 46, Nos. 1 & 2, (1994).
Side effects listed on product label for Fer-In-Sol® Iron Supplement, Enfamil® Fer-in-Sol®, Taken from website: www.meadjohnson.com, 2009.
Ullrich et al, Screening Healthy Infants for Iron Deficiency Using Reticulocyte Hemoglobin Content, JAMA, vol. 294, No. 8, pp. 924-930, (Aug. 2005).

(Continued)

*Primary Examiner* — Abigail Fisher
(74) *Attorney, Agent, or Firm* — Cathy A. Kodroff; Howson & Howson LLP; Egon Berg

(57) ABSTRACT

A process for preparing a formulation comprising a complex comprising an effective amount of ferrous iron bound to a pharmaceutically acceptable cationic resin and at least one pharmaceutically acceptable carrier is described. Such a formulation may optionally include other desirable dietary supplements including, e.g., vitamins, omega fatty acids, and/or fluoride. The formulation is particularly well adapted for pediatric use, but is also useful for use in adult populations.

24 Claims, No Drawings

OTHER PUBLICATIONS

Amendment filed on May 25, 2011 in corresponding U.S. Appl. No. 11/724,966.
Amendment filed on Oct. 14, 2010 in corresponding U.S. Appl. No. 11/724,966.
Amendment filed on Sep. 23, 2010 in corresponding U.S. Appl. No. 11/724,966.
Final Office Action dated Jun. 23, 2010 in corresponding U.S. Appl. No. 11/724,966.
Non-Final Office Action dated Nov. 12, 2009 in corresponding U.S. Appl. No. 11/724,966.
Response to Restriction dated Jul. 29, 2009 in corresponding U.S. Appl. No. 11/724,966.
Office Action dated Jun. 1, 2009 in corresponding U.S. Appl. No. 11/724,966.
Tris Pharma, Inc., MyKidzIronFL™, Prescribing information, Liquid Iron Suspension with Vitamins A, C, D, and Fluoride, Mar. 1, 2011.
Tris Pharma, Inc., MyKidz Iron™ Supplements, Product Facts and Wholesale Order Form, 2011.
Mehta, et al., U.S. Appl. No. 12/261,349, filed Oct. 20, 2008.
Office Action dated Aug. 24, 2011 and Response of Nov. 2, 2011 in U.S. Appl. No. 12/261,349 (item 35).
Mehta, et al, U.S. Appl. No. 12/154,970, filed May 28, 2008.
Mehta, et al, U.S. Appl. No. 12/908,796, filed Oct. 20, 2010.
Mehta, et al, U.S. Appl. No. 13/244,706, filed Sep. 26, 2011.
Mehta, et al, U.S. Appl. No. 13/244,748, filed Sep. 26, 2011.

* cited by examiner

FORMULATIONS CONTAINING AN IONIC MINERAL-ION EXCHANGE RESIN COMPLEX AND USES THEREOF

CROSS-REFERENCE TO RELATED APPLICATIONS

This is a national stage application under 35 USC §371 of PCT/US2007/020844, filed on Sep. 27, 2007, which claims the benefit under 35 USC §119(e) of the priority of U.S. Provisional Patent Application No. 60/827,974, filed Oct. 3, 2006.

BACKGROUND OF THE INVENTION

The present invention relates to a formulation having a mineral-ion exchange resin complex that is useful as a dietary supplement.

A variety of commercial products are available which have been described as being useful as dietary supplements and/or for treatment of certain mineral and vitamin deficiencies. Such products have been formulated for either pediatric delivery (infants and children) or for adults (including the geriatric population). Depending upon the target population, such products are available as liquid suspensions, powders, tablets and/or other solid forms. Certain of these products, including, notably, those containing iron supplements in liquid form, have been reported to have undesirable side effects including, e.g., gastric irritation and stomach upset, staining of teeth, and a less than desirable taste. See, e.g., side effects listed on product label for Fer-In-Sol® iron supplement [Mead Johnson], "Pharmacy and Therapeutics Committee Medication Review, May 21, 2004, citing Drug Facts and Comparisons, updated November 2003.

Use of ion-exchange resins to form a drug-ion exchange resin complex is well known and is described, for example, in U.S. Pat. No. 2,990,332. In the '332 patent, the use of an ion-exchange resin to form a complex with ionic drugs and thereby delay the drug release from such complexes is described. Such delay in drug release was deemed to be of relatively short duration. Since then there have been additional publications and patents (e.g., U.S. Pat. Nos. 3,138,525; 3,499,960; 3,594,470; Belgian patent 729,827; German patent 2,246,037) that describe use of such ion-exchange resin complexes with water-permeable diffusion barrier coatings of the drug-ion exchange resin complex coated to alter the release of drugs from the drug-ion exchange resin complex. Ion-exchange resin complexes have also been described by their manufacturers and in the literature as being useful for taste masking of unpleasant tasting drugs [Rohm and Haas].

Additionally, analysis of the iron state in some iron-containing vitamins and dietary supplements has revealed higher amounts of ferric impurities than is desirable or permitted under FDA standards. See, Oshtrack et al, *Analytica Chimica Acta,* 506 (2004) 155-160. This article reports that due to concerns regarding toxicity of ferric iron, the FDA has indicated the ferrous fumarate dietary supplements should not contain more than 2% ferric iron. The article also reports that several marketed formulations tested off the shelf have been found to have higher ferric contents that permitted by the FDA due to oxidation.

Alternatives to the formulations currently on the market for dietary supplements are desirable.

SUMMARY OF THE INVENTION

In one aspect, a method of manufacture of liquid suspensions comprising ionic mineral-ion exchange resin complexes is provided that reduces oxidation of the ionic mineral and improves yield. The method permits formation of the final liquid suspension in the same vessel as the ionic mineral-ion exchange complex is formed, without requiring isolation thereof.

In another aspect, a non-toxic, orally ingestible mineral-ion exchange resin formulation useful as a dietary supplement is provided. The formulation comprises a complex comprising an effective amount of an ionic mineral bound to a pharmaceutically acceptable ion exchange resin; and at least one pharmaceutically acceptable carrier.

In another aspect, the invention provides a formulation contains a complex comprising an effective amount of ferrous iron bound to a pharmaceutically acceptable cationic resin and at least one pharmaceutically acceptable carrier. Suitably, the formulation further comprises an antioxidant. In one embodiment, the composition is formulated for pediatric use.

In yet another aspect, the invention provides a composition comprising (a) non-toxic, orally ingestible mineral-ion exchange resin complex comprising an effective amount of an ionic mineral bound to a pharmaceutically acceptable ion exchange resin; (b) a vitamin; (c) a fluoride compound; and (d) at least one pharmaceutically acceptable carrier.

In still another aspect, the invention provides a method of delivering an ionic mineral to a subject, via the ionic mineral-ion exchange resin complex of the invention.

In yet a further aspect, the invention provides a method of treating iron deficiency comprising the step of administering an effective amount of a non-toxic, orally ingestible iron-ion exchange resin formulation comprising a complex comprising a pharmaceutically effective amount of an ionic mineral component bound to a pharmaceutically acceptable ion exchange resin, and a pharmaceutically acceptable carrier.

The invention advantageously provides a reduction of undesirable tastes sometimes associated with an orally ingestible vitamin formulation, where unpleasant taste of the ionic mineral may be a detriment for compliance with the recommended daily intake.

Still other aspects and advantages of the invention will be readily apparent from the following detailed description.

DETAILED DESCRIPTION OF THE INVENTION

The present invention provides an ionic mineral-ion exchange resin formulation useful for delivery to a subject as a dietary supplement, or for therapeutic or prophylactic purposes. The formulation contains a complex comprising an effective amount of an ionic mineral bound to a pharmaceutically acceptable ion exchange resin; and at least one pharmaceutically acceptable carrier.

As used herein, "an effective amount" refers to an amount of a component, e.g., an ionic mineral, which provides a nutritional or pharmaceutical benefit to the subject to which it is administered in a single or multiple units.

The term "ionic mineral" refers to an element or electrolyte, which carries a positive or negative charge. Desirably, the ionic minerals described herein are those which are useful for the functioning of the body's cells. In one embodiment, the ionic mineral is iron. Other examples of such ionic minerals include, e.g., sodium, potassium, calcium, magnesium, chloride, and phosphate. These minerals are called macrominerals, since large quantities are required by the body. The body also needs small quantities of copper, fluoride, iodine, iron, selenium, and zinc. These minerals are called trace minerals. Some minerals—especially the macrominerals— are important as electrolytes. The body uses electrolytes to help regulate nerve and muscle function and acid-base balance. Also, electrolytes help the body maintain normal volume in its different fluid-containing areas (compartments). Other ionic minerals include, without limitation, boron, chromium, cobalt, germanium, gold, nickel, silver, iodine, molybdenum, platinum, sulfur, tin, vanadium. Still other suitable ionic minerals will be readily apparent to one of skill in the art. For example, one may select lithium for inclusion in a resin complex as described herein.

Suitably, the source of the ionic mineral is a compound which contains the ionic mineral bound or complexed to a moiety from which it readily dissociates in a non-ionic, physiologically compatible diluent so as to permit the ionic mineral to bind to the ionic resin and which is dissociated from a donor element or moiety which is not physiologically detrimental or incompatible with other components of the suspension. Optionally, the freed moiety may itself be physiologically useful (e.g., a sulfur compound). Suitable compounds can be found in the scientific literature; additionally, many such compounds are commercially available. Examples of suitable compounds include a salt, such as a sulfate, a carbonate, an ascorbate, a citrate, or the like, of the ionic molecule, may be readily selected. Alternatively, the ionic mineral may be bound to another salt or another moiety. For example, if the ionic mineral is iron, the source of the compound is desirably ferrous sulfate, which readily dissociates and which provides freed sulfate. However, other donor sources of iron may be readily selected including, e.g., a ferrous fumarate, a polymaltose, a bisglycinate, ferrous glycine sulphate, ferrous gluconate, ferrous citrate, ferrous carbonate, ferrous lactate, ferrous succinate, ferrous ascorbate, an amino acid ferrous complex, or a hydrate thereof. Donor sources for other ionic minerals including, e.g., ferric iron or another ionic mineral described herein, will be readily apparent to one of skill in the art.

Suitable dietary intakes for various minerals and vitamins can be readily obtained from the Food and Nutrition Board of the National Academy of Sciences, taking into consideration whether the target population is pediatric or adult and other relevant factors within the adult population, including, gender, pregnancy, lactating, over 51. For example, for iron, recommended daily amounts are:

| Age (years) or status | RDA mg/day | |
|---|---|---|
| 0.0 to 0.5 | 6 | |
| 0.5 to 1.0 | 10 | |
| 1 to 3 | 10 | |
| 4 to 6 | 10 | |
| 7-10 | 10 | |
| | Males | Females |
| 11-14 | 12 | 15 |
| 15-18 | 12 | 15 |
| 19-24 | 10 | 15 |
| 25-50 | 10 | 15 |
| 51 and over | 10 | 10 |
| Pregnant | — | 30 |
| Lactating | — | 15 |

Guidelines are also provided for the dietary reference intakes available from the Food and Nutrition Board for elements, e.g., calcium, chromium, magnesium, phosphorus, fluoride, manganese, zinc, selenium, electrolytes including, e.g., sodium, potassium, and inorganic sulfate, and vitamins including, e.g., Vitamin A, Vitamin C, Vitamin D, Vitamin $B_3$ [known as niacin, and also available as nicotinic acid and pharmaceutically acceptable salts thereof], Vitamin $B_6$, Vitamin $B_{12}$, Vitamin E and Vitamin K. Other desirable nutrient components for dietary supplements may include folate, (or its synthetic form, folic acid, or pharmaceutically acceptable salts thereof), and omega-3-fatty acids.

As used herein in reference to numeric values provided herein, the term "about" may indicate a variability of as much as ±10%.

Ion-Exchange Resin

Contemplated within the scope of the invention are important nutrients and pharmaceutically active compounds safe for ingestion, which form a complex with an ion-exchange resin and are manufactured in accordance with Good Manufacturing Practices (GMP) for bulk pharmaceutical chemicals. Typically, these compounds are designed for oral administration and administration via a gastric and/or nasogastric tube.

Ion-exchange resins suitable for use in these preparations are water-insoluble and comprise a preferably pharmacologically inert organic and/or inorganic matrix containing functional groups that are ionic or capable of being ionized under the appropriate conditions of pH. The organic matrix may be synthetic (e.g., polymers or copolymers of acrylic acid, methacrylic acid, sulfonated styrene, sulfonated divinylbenzene), or partially synthetic (e.g. modified cellulose and dextrans). The inorganic matrix preferably comprises silica gel modified by the addition of ionic groups. Covalently bound ionic groups may be strongly acidic (e.g., sulfonic acid, phosphoric acid), weakly acidic (e.g., carboxylic acid), strongly basic (e.g., primary amine), weakly basic (e.g. quaternary ammonium), or a combination of acidic and basic groups. In general, the types of ion exchangers suitable for use in ion-exchange chromatography and for such applications as deionization of water are suitable for use in the controlled release of drug preparations. Such ion-exchangers are described by H. F. Walton in "Principles of Ion Exchange" (pp: 312-343) and "Techniques and Applications of on-Exchange Chromatography" (pp: 344-361) in Chromatography. (E. Heftmann, editor), van Nostrand Reinhold Company, New York (1975). Ion exchange resins that can be used in the present invention have exchange capacities of about 6 milliequivalents (meq)/gram and preferably about 5.5 meq/gram or below.

Typically the size of the ion-exchange particles is from about 1 micron to about 900 microns, in another embodiment, about 5 microns to 750 microns, and in yet another embodiment, the particle size is within the range of about 40 microns to about 250 microns for liquid dosage forms although particles up to about 1,000 micron can be used for solid dosage forms, e.g., tablets and capsules. Particle sizes substantially below the lower limit are generally difficult to handle in all steps of the processing.

Both regularly and irregularly shaped particles may be used as resins. Regularly shaped particles are those particles that substantially conform to geometric shapes such as spherical, elliptical, cylindrical and the like, which are exemplified by Dow XYS-40010.00 and Dow XYS-40013.00 (The Dow Chemical Company). Irregularly shaped particles are all particles not considered to be regularly shaped, such as particles with amorphous shapes and particles with increased surface areas due to surface channels or distortions. Irregularly shaped ion-exchange resins of this type are exemplified by Amberlite IRP-69 (Rohm and Haas). Two of the preferred resins useful in this invention are Amberlite IRP-69 and Dow XYS-40010.00. Both are sulfonated polymers composed of polystyrene cross-linked with about 8% of divinylbenzene, with an ion-exchange capacity of about 4.5 to 5.5 meq/g of dry resin ($H^+$-form). Their essential difference is in physical form. Amberlite IRP-69 consists of irregularly shaped particles with a size range of about 5 microns to about 149 microns produced by milling the parent large size spheres of Amberlite IRP-120. The Dow XYS-40010.00 product consists of spherical particles with a size range of 45 microns to 150 microns. Other suitable ion-exchange resins include anion exchange resins, such as have been described in the art and are commercially available.

Cation exchange resins, e.g., AMBERLITE IRP-69, Amberlite IRP-64, Amberlite IRP-88 (Rohm & Haas), Dowex 50 W resin (Dow), C100MR, C100HMR, C115KMR (Purolite), are particularly well suited for use with cationic minerals and other molecules having a cationic functionality, including, e.g., ferrous iron, ferric iron, potassium, sodium, calcium, lithium, zinc, magnesium, and selenium (in certain embodiments) as well as prodrugs, salts, isomers, polymorphs, and solvates thereof, as well as other minerals identified herein and/or known in the art. Cationic exchange resins are readily selected for use of these cationic minerals identified herein and/or are those which are known to those of skill in the art.

Selenium has been described as having a valence of +2 or −2 depending upon whether it is present as selenium (+2) (e.g., a selenium dioxide, selenic acid, selenous acid, selenium sulfide) or a selenite or selenide (e.g., sodium selenite, zinc selenide). Depending upon the source donor compound, selenium may be complexed with a cationic exchange resin (e.g., if selenium dioxide is the source compound), or with an anionic exchange resin (e.g., if sodium selenite) is the source compound.

Anion exchange resins are useful in conjunction with anionic minerals, e.g., certain embodiments of selenium. An example of an anion exchange resin is a cholestyramine resin, a strong base type 1 anion exchange resin powder with a polystyrene matrix and quarternary ammonium functional groups. The exchangeable anion is generally chloride which can be exchanged for, or replaced by, virtually any anionic species. A commercially available Cholestyramine resins is PUROLITE™ A430MR resin. As described by its manufacturer, this resin has an average particle size range of less than 150 microns, a pH in the range of 4-6, and an exchange capacity of 1.8-2.2 eq/dry gm. Another pharmaceutical grade cholestyramine resin is available as DUOLITE™ AP143/1094 [Rohm and Haas], described by the manufacturer as having a particle size in the range of 95%, less than 100 microns and 40%, less than 50 microns. The commercial literature from the suppliers of these and other resin is incorporated herein by reference (PUROLITE A-430 MR; DOW Cholestyramine USP, Form No. 177-01877-204, Dow Chemical Company; DUOLITE AP143/1083, Rohm and Haas Company, IE-566EDS—February 2006).

The selected ion-exchange resins may be further treated by the manufacturer or the purchaser to maximize the safety for pharmaceutical use or for improved performance of the compositions. Impurities present in the resins may be removed or neutralized by the use of common chelating agents, antioxidants, preservatives such as disodium edetate, sodium bisulfite, and so on by incorporating them at any stage of preparation either before complexation or during complexation or thereafter. These impurities along with their chelating agent to which they have bound may be removed before further treatment of the ion exchange resin Ionic Mineral—Ion Exchange Resin Complexes Binding of the selected ionic mineral(s) or combination of ionic mineral(s) and another component to the ion exchange resin can be accomplished using methods known in the art. Typically the ionic mineral-ion exchange resin complex thus formed is collected by filtration and washed with appropriate solvents to remove any ionic mineral or by-products. The complexes can be air-dried in trays, in a fluid bed dryer, or other suitable dryer, at room temperature or at elevated temperature.

For preparing the complexes, the batch equilibration is the preferred practice when loading a ionic mineral into finely divided ion exchange resin powders. Due to its fine particle size, ion exchange resin does not lend itself to conventional columnar operations used with ion exchange resins. The total ion exchange capacity represents the maximum achievable capacity for exchanging cations or anions measured under ideal laboratory conditions. The capacity which will be realized when loading an ionic mineral onto ion exchange resin will be influenced by such factors as the inherent selectivity of the ion exchange resin for the ionic mineral, the ionic mineral's concentration in the loading solution and the concentration of competing ions also present in the loading solution. The rate of loading will be affected by the activity of the ionic mineral and its molecular dimensions as well as the extent to which the polymer phase is swollen during loading.

When utilizing a batch or equilibrium process for loading an ionic mineral onto an ion exchange resin, it is usually desirable to load as much as possible of the substance of value onto the ion exchange resin. Complete transfer of the ionic mineral from the loading solution is not likely in a single equilibrium stage. Accordingly, more than one equilibration may be required in order to achieve the desired loading onto the ion exchange resin. The use of two or more loading stages, separating the resin from the liquid phase between stages, is a means of achieving maximum loading of the ionic mineral onto the ion exchange resin although loss of ionic mineral from the liquid phase of the final stage occurs.

Although carefully controlled laboratory experiments are required to establish precise loading and elution conditions, a few general principles can be used. High loading capacity will be favored by high charge density in the ionic mineral. A high loading rate is favored by lower molecular weight. Higher ionic mineral concentrations in the loading solution, with a minimum of competing ions, will also favor higher adsorption capacity.

The amount of ionic mineral that can be loaded onto a resin will typically range from about 1% to about 70% by weight of the ionic mineral-ion exchange resin particles, preferably about 1 to 50% by weight. A skilled artisan with limited experimentation can determine the optimum loading for any ionic mineral-resin complex. In one embodiment, loading of about 10% to about 40% by weight, more desirably, about 15% to about 30% by weight, of the ionic mineral-ion exchange resin particles can be employed. Typical loadings of about 25% by weight of the ionic mineral to ion exchange resin particles can be advantageously employed. In one embodiment, e.g., if the amount of ionic mineral is loaded at the lower end of this range, i.e., about 1% to about 15%, or about 5% to about 10%, or the like, the amount of ionic mineral-ion exchange resin particles in the final formulation can be adjusted to provide the appropriate effective amount of the ionic mineral. However, this may result in a larger dosage unit, or in the need for increased dosages to obtain the desired effective amount. In another embodiment, more than one ionic mineral is present in the resin complex. In such case, the total amount of ionic minerals is within the ranges provided herein, with each ionic mineral preferably also falling within these ranges.

Typically, the resin is mixed with a suitable diluent in an amount of about 1 to 50% w/v of the mixture. In one embodiment, the resin is about 5 to about 30% w/w of the mixture. In another embodiment, the resin is about 10 to 25% w/v of the mixture. In still another embodiment, the resin is about 5 to 10% w/v of the mixture. However, other suitable amounts of the resin may be readily selected.

Typically, the resin is present in an amount of about 30% to about 99% w/w, more preferably about 30% w/w to about 95% w/w, about 60% w/w to about 90% w/w, or about 85% to about 70% w/w of the ionic mineral-ion exchange resin complex. However, these amounts may be adjusted as needed or desired, if additional components are bound in the ionic mineral-ion exchange resin complex. In one embodiment, no other active pharmaceutical or nutritional ingredients or components are included. In another embodiment, another nutritional or pharmaceutically active component is included. In still another embodiment, the active component is a drug.

In one embodiment, an antioxidant is included in the mixture at the time the source compound of the ionic mineral is combined with the complexing agent (i.e., resin) in a suitable diluent. In one embodiment, an antioxidant functions to stabilize the ionic mineral. For example, an antioxidant minimizes conversion of ferrous iron to ferric iron, which is desirable since ferrous iron has been described in the literature as being better absorbed by the body. However, even where antioxidant is present, some minimal amount of conversation to ferric ion can be tolerated.

Typically, an antioxidant is present in amount of about 0.05 to about 2% w/v, and more preferably in an amount of about 0.05 to 0.2% w/v. Suitable antioxidants may be readily selected from among, e.g., ascorbic acid and pharmaceutically acceptable salts thereof, sodium metabisulfite, sodium bisulfite, sodium sulfite, potassium metabisulfite, sodium ascorbate, tocopherol, propyl gal late, butylated hydroxyanisole, butylated hydroxytoluene, edetic acid and its salts. In one embodiment, the antioxidant is ascorbic acid or a pharmaceutically acceptable salt thereof.

The antioxidant may be present in a higher amount. For example, ascorbic acid or a pharmaceutically acceptable salt thereof may be utilized as an antioxidant within the ranges provided herein. Alternatively, the ascorbic acid or salt may be present in higher amounts in order to provide an effective amount of Vitamin C. In this embodiment, the ascorbic acid may be present in an amount in excess of 2% w/v, e.g., about 2.5% w/v to 10% w/v, or about 3.5% to 5% w/v. Following formation of the ionic mineral-ion exchange resin complex in a reaction mixture, antioxidant and diluent may be removed.

Thus, in one aspect, the invention provides ionic mineral-ion exchange resin complexes comprising an ionic mineral loaded in an ion exchange resin as described herein.

Finished Dose Formulations

The ionic mineral-ion exchange resin complexes of the present invention, can readily be formulated with pharmaceutically acceptable excipients according to methods well known to those of skill in the art. In desirable embodiment, the formulations contain an antioxidant. The formulations of the invention may contain more than one dietary supplement or another component. For example, the formulation may contain more than one ionic mineral loaded into an ion exchange resin to form a complex of the invention. As another example, the formulation may contain a first ionic mineral-ion exchange resin complex of the invention in combination with another dietary supplement which may be in a second ionic mineral-ion ion exchange resin complex of the invention. In still another example, the formulation may contain an ionic mineral-ion exchange resin complex of the invention in combination with one or more components which are not in an ionic mineral-ion exchange resin complex.

The ionic mineral-ion exchange resin complex of the invention may be formulated for delivery by any suitable route including, e.g., orally, intraperitoneally, sublingually, intramuscularly, rectally, transbuccally, intranasally, liposomally, via inhalation, vaginally, intraoccularly, via local delivery (for example, by catheter or stent), subcutaneously, intraadiposally, intraarticularly, or intrathecally. Preferably, the complex is formulated for oral delivery.

The ionic mineral-ion exchange resin composition thus prepared may be stored for future use or promptly formulated with conventional pharmaceutically acceptable carriers to prepare finished ingestible compositions for delivery orally, gastric tube, nasogastric tube, or via other means. The compositions according to this invention may, for example, take the form of liquid preparations such as suspensions, or solid preparations such as capsules, tablets, caplets, sublinguals, powders, wafers, strips, gels, including liquigels, etc. In one embodiment, a tablet of the invention is formulated as an orally disintegrating tablet. Such orally disintegrating tablets may disintegrate in the mouth in less than about 60 seconds.

The ionic mineral-ion exchange resin compositions may be formulated using conventional pharmaceutically acceptable carriers or excipients and well established techniques. In the present invention, ingestible carriers are particularly desirable and include liquids and food product. The ionic mineral-ion exchange resins can be mixed with such ingestible liquids or food products, and, optionally used for fortification of pre-packaged liquids and food products. Further, without being limited thereto, such conventional carriers or excipients include aqueous and non-aqueous diluents, binders and adhesives (i.e., cellulose derivatives and acrylic derivatives), lubricants (i.e., magnesium or calcium stearate, or vegetable oils, polyethylene glycols, talc, sodium lauryl sulfate, polyoxy ethylene monostearate), thickeners, solubilizers, humectants, disintegrants, colorants, flavorings, stabilizing agents, sweeteners, and miscellaneous materials such as buffers and adsorbents in order to prepare a particular pharmaceutical composition. The stabilizing agents may include preservatives and anti-oxidants, amongst other components which will be readily apparent to one of ordinary skill in the art. In one embodiment where the ionic mineral is a ferrous-cationic exchange resin complex, the finished formulation preferably contains an antioxidant which retards oxidation of the ferrous ion to ferric ion. This is desirable due to the absorption of ferrous iron, as compared to ferric iron.

Suitable thickeners include, e.g., tragacanth; xanthan gum; bentonite; starch; acacia and lower alkyl ethers of cellulose (including the hydroxy and carboxy derivatives of the cellulose ethers). Examples of cellulose include, e.g., hydroxypropyl cellulose, hydroxypropyl methyl cellulose, sodium carboxy methylcellulose, microcrystalline cellulose (MCC), and MCC with sodium carboxyl methyl cellulose. In liquid formulations, such thickening agents may function as suspending agents which can be used alone or in combinations. Exemplary suspending agents may include starch instant clearjel and xanthan gum. Starch instant clearjel may be used in the amount of from about 0.1 to about 10% w/v and preferably about 2 to about 3% w/v. Xanthan gum is used in the amount of from about 0.01 to about 5% w/v and preferably about 0.1-0.3% w/v. For solid formulations, particularly desirable bulking agents include mannitol and microcrystalline cellulose. Other suitable thickeners, also termed bulking agents, are readily selected from amongst those components described herein as a cellulose and from those known in the art. Bulking agents may be used alone or in combination in an amount of about 5% w/w to a total amount of up to about 90% w/w, preferably about 10% w/w to a total amount of up to about 70% w/w, more preferably about 10% w/w to about 50% w/w, most preferably about 10% to about 30% w/w. In one embodiment, mannitol and/or microcrystalline cellulose may be used in an amount of about 10% w/w to about 15% w/w. When used in combination, they may be present in a ratio of 1:1 w/v or one more be present in a higher amount than another.

The ionic mineral-ion exchange resin compositions may include a component which gives the liquid greater viscosity and stability. Suitable components for this purpose include, e.g., glycerin, polyethylene glycol, propylene glycol and mixtures thereof. For example, in one embodiment, a solubilizer may be present in the amount of 1 to 50% w/v, and preferably, about 5 to 15% w/v. In one embodiment, the solubilizer is glycerin.

The oral liquid compositions of the present invention may also comprise one or more surfactants in amounts of up to about 15% w/v, preferably from about 1 to 3% w/v, and more preferably about 0.1 to about 0.5% w/v of the total formulation. The surfactants useful in the preparation of the finished compositions of the present invention are generally organic materials which aid in the stabilization and dispersion of the ingredients in aqueous systems for a suitable homogenous composition. Preferably, the surfactants of choice are non-ionic surfactants such as poly(oxyethylene)(20) sorbitan monooleate and sorbitan monooleate. These are commercially known as TWEENS and SPANS and are produced in a wide variety of structures and molecular weights.

A compound from the group comprising polysorbate copolymers (sorbitan-mono-9-octadecenoate-poly(oxy-1,2-ethanediyl)) can be employed as a surfactant. This compound is also added functions to keep any flavors and sweeteners homogeneously dissolved and dispersed in solution. Other suitable polysorbates include polysorbate 20, polysorbate 40, polysorbate 80 and mixtures thereof. Most preferably, polysorbate 80 is employed. The surfactant component will comprise from about 0.01 to about 2% w/v of the total composition and preferably will comprise about 0.5 to about 0.6% w/v of the composition.

A second emulsifier/surfactant useful in combination with polysorbates may be employed, e.g., a poloxamer such as Poloxamer 407. Poloxamer 407 has an HLB (hydrophilic/lipophilic balance) of about 22 and is sold under the tradename Pluronic-127 (BASF-NJ). The two surfactants can be employed in substantially equivalent amounts.

Aqueous suspensions may be obtained by dispersing the ionic mineral-ion exchange resin compositions in a suitable aqueous vehicle, optionally with the addition of suitable viscosity enhancing agent(s) (e.g., cellulose derivatives, xanthan gum, etc). Non-aqueous suspensions may be obtained by dispersing the foregoing compositions in a suitable non-aqueous based vehicle, optionally with the addition of suitable viscosity enhancing agent(s) (e.g., hydrogenated edible fats, aluminum state, etc.). Suitable non-aqueous vehicles include, for example, almond oil, arachis oil, soybean oil or soybean oil or fractionated vegetable oils such as fractionated coconut oil.

Suitably, a buffer may be included in the vehicle (e.g., purified water). Suitable buffers are well known to those of skill in the art and may include, e.g., citric acid, tartaric acid, phosphoric acid, acetic acid, and their respective salts. Where utilized, e.g., citric acid, the buffer may be present in an amount of about 0.1 to 2% w/v, preferably about 0.1 to about 0.5% w/v of the composition.

Useful preservatives include, but are not limited to, sodium benzoate, benzoic acid, potassium sorbate, salts of edetate (also known as salts of ethylenediaminetetraacetic acid, or EDTA, such as disodium EDTA), parabens (e.g., methyl, ethyl, propyl or butyl-hydroxybenzoates, etc.), and sorbic acid. Amongst useful preservatives include chelating agents some of which are listed above and other chelating agents, e.g., nitrilotriacetic acid (NTA); ethylenediaminetetracetic acid (EDTA), hydroxyethylethylenediaminetriacetic acid (HEDTA), diethylenetriaminepentaacetic acid (DPTA), 1,2-Diaminopropanetetraacetic acid (1,2-PDTA); 1,3-Diaminopropanetetraacetic acid (1,3-PDTA); 2,2-ethylenedioxybis [ethyl iminodi(acetic acid)] (EGTA); 1,10-bis(2-pyridylmethyl)-1,4,7,10-tetraazadecane (BPTETA); ethylenediamine (EDAMINE); Trans-1,2-diaminocyclohexane-N,N,N',N'-tetraacetic acid (CDTA); ethylenediamine-N,N'-diacetate (EDDA); phenazine methosulphate (PMS); 2,6-Dichloro-indophenol (DCPIP); Bis(carboxymethyl)diaza-18-crown-6 (CROWN); porphine; chlorophyll; dimercaprol (2,3-Dimercapto-1-propanol); citric acid; tartaric acid; fumaric acid; malic acid; and salts thereof. The preservatives listed above are exemplary, but each preservative must be evaluated in each formulation, to assure the compatibility and efficacy of the preservative. Methods for evaluating the efficacy of preservatives in pharmaceutical formulations are known to those skilled in the art. Preferred preservatives are the paraben preservatives include, methyl, ethyl, propyl, and butyl paraben. Methyl and propyl paraben are most preferable. Preferably, both methyl and propyl paraben are present in the formulation in a ratio of methyl paraben to propyl paraben of from about 2.5:1 to about 16:1, preferably 9:1.

In the instance where auxiliary sweeteners are utilized, the present invention contemplates the inclusion of those sweeteners well known in the art, including both natural and artificial sweeteners. Thus, additional sweeteners may be chosen from the following non-limiting list: Water-soluble sweetening agents such as monosaccharides, disaccharides and polysaccharides such as xylose, ribose, glucose, mannose, galactose, fructose, high fructose corn syrup, dextrose, sucrose, sugar, maltose, partially hydrolyzed starch, or corn syrup solids and sugar alcohols such as sorbitol, xylitol, mannitol and mixtures thereof;

In general, the amount of sweetener will vary with the desired amount of sweeteners selected for a particular formulation. This amount will normally be 0.001 to about 90% by weight, per volume of the final composition, when using an easily extractable sweetener. Depending upon the selected sweetener, the sweetener is present at the higher end of this range for liquid suspensions and at the lower end of the range (or absent) in solid formulations. The water-soluble sweeteners described above, are preferably used in amounts of about 5 to about 80% by weight per volume, and most preferably from about 20 to about 40% by weight per volume of the final liquid composition. In contrast, the artificial sweeteners [e.g., sucralose, acesulfame K, and dipeptide based sweeteners] are used in amounts of about 0.005 to about 5.0% w/v, about 1-2% w/v, preferably about 0.03 to about 1.1% w/v, more preferably about 0.4 to about 0.6% w/v of the final liquid composition, or about 0.2 to about 0.5% w/w of a solid formulation (e.g., an orally disintegrating tablet). These amounts are ordinarily necessary to achieve a desired level of sweetness independent from the flavor level achieved from flavor oils.

Suitable flavorings include both natural and artificial flavors, and mints such as peppermint, menthol, artificial vanilla, cinnamon, various fruit flavors, both individual and mixed, essential oils (i.e. thymol, eucalyptol, menthol and methyl salicylate) and the like are contemplated. The amount of flavoring employed is normally a matter of preference subject to such factors as flavor type, individual flavor, and strength desired. Thus, the amount may be varied in order to obtain the result desired in the final product. Such variations are within the capabilities of those skilled in the art without the need for undue experimentation. The flavorings are generally utilized in amounts that will vary depending upon the individual flavor, and may, for example, range in amounts of about 0.01 to about 3% by weight per volume of the final composition weight.

The colorants useful in the formulations described herein include the pigments such as titanium dioxide, that may be incorporated in amounts of up to about 1% by weight per volume, and preferably up to about 0.6% by weight per volume. Also, the colorants may include dyes suitable for food, drug and cosmetic applications, and known as D&C and F.D. & C. dyes and the like. The materials acceptable for the foregoing spectrum of use are preferably water-soluble. Illustrative examples include indigoid dye, known as F.D. & C. Blue No. 2, which is the disodium salt of 5,5'indigotindisulfonic acid. Similarly, the dye known as F.D. & C. Green No. 1 comprises a triphenylmethane dye and is the monosodium salt of 4-[4-N-ethyl p-sulfobenzylamino)diphenylmethylene]-[1-(N-ethyl-N-p-sulfonium benzyl)-2,5-cyclohexadienimine]. A full recitation of all F.D. & C. and D. & C. and their corresponding chemical structures may be found in the Kirk-Othmer Encyclopedia of Chemical Technology, in Volume 5, at Pages 857-884, which text is accordingly incorporated herein by reference.

Wetting agents also may be employed in the inventive compositions to facilitate the dispersion of any hydrophobic ingredients. The concentration of wetting agents in the composition should be selected to achieve optimum dispersion of the ingredient within the composition with the lowest feasible concentration of wetting agent. It should be appreciated that an excess concentration of wetting agent may cause the composition, as a suspension, to flocculate. Those skilled in the art are well versed in suitable empirical methods to determine the appropriate wetting agents and concentrations to achieve optimum dispersion and avoid flocculation. Suitable wetting agents are listed in the US Pharmacoepia 29.

Preparation of Liquid Formulations

In one aspect, a novel method of preparing a liquid formulation useful as a dietary supplement comprising a non-toxic, orally ingestible, mineral-ion exchange resin complex is provided. This method involves forming a mixture comprising an ionic mineral compound, a pharmaceutically acceptable ion-exchange resin, and the suspension base whereby a complex comprising the ionic mineral bound to the ion exchange resin complex is formed in situ. Advantageously, this process eliminates the need for isolation of the ionic mineral-resin complex. This permits all ingredients to be added and processed in the same container, reducing the exposure of the ionic mineral to the risk of oxidation. This process enhances the efficiency of total process time and increases the yield due to consolidated processing steps which eliminate the need for filtration, purification, isolation and drying of the complex into a powder or other dried form. In one particularly desirable embodiment, the wet complex is formulated as a liquid suspension.

In order to form the reaction mixture, a donor compound which is the source of the ionic mineral is added to a suitable diluent (e.g., purified water) or another physiologically compatible diluent. Typically, the water is a deionized or purified water. In one embodiment, an antioxidant and/or a pH adjuster is included in the mixture/solution when the ionic mineral source compound is combined with the resin in the diluent. One example of an antioxidant is ascorbic acid or a pharmaceutically acceptable salt thereof.

Typically, the ion exchange resin complex is added to the solution comprising the ionic mineral and optional antioxidant and pH adjuster and the reaction mixture is stirred to allow the ionic mineral-ion exchange resin complex to form. The reaction can be performed at room temperature for a period of, e.g., 1 to 4 hours. However, longer or shorter times may be used where desired. In another embodiment, the reaction can be performed temperatures higher than room temperature in order to increase the rate of the reaction.

Desirable components, including antioxidant, excipients, fluoride, pH adjusters, etc., may be added to the mixture prior to the reaction between the donor compound of the ionic mineral and the ion exchange resin complex, at the same time, or following formation of the complex. In one embodiment, the suspension base is added to the mixture following a reaction time in which the complex is permitted to form. Optionally, other components such as vitamins, fluoride, omega fatty acids, may be added to the mixture following formation of the complex, or at the same time.

In another embodiment, one or more of the components of a suspension base may be added to the mixture at substantially the same time as the other components or prior to the formation or completion of the complex formation. Typical components of a suspension base (sometimes termed a placebo suspension base) include those liquid carriers, flavoring agents, thickeners, preservatives, etc., examples of which are described herein, which provide desirable taste and suspension properties to a finished orally ingestable, liquid suspension formulation. In this embodiment, the reaction is generally permitted additional time in order to permit complex formation.

Optionally, following formation of the ionic mineral-ion exchange resin complex, the slurry may be rinsed and/or filtered, prior to addition of the final suspension base.

In one aspect, a finished formulation contains at least one ionic mineral-ion exchange resin complex, optionally in combination with at least one selected from amongst minerals, vitamins (e.g., the Vitamin B family, Vitamin K, and Vitamin E, etc.) amino acids, omega fatty acids, a nutrient, or another component.

Suitable amounts of the ionic minerals, vitamins, and like provided herein can be readily determined taking into consideration these guidelines for the recommended daily intake of each. When used as a dietary supplement, a formulation is useful for supplementing the nutrient intake of the diet, and is preferably taken by mouth (orally). Such a formulation may include, in addition to the ionic mineral-iron exchange resin complex, one or more other minerals, vitamins, herbs, botanicals, amino acids, or omega-3-fatty acids, and other components which are not complexed with an ion-exchange resin. Optionally, ionic mineral source compounds and/or uncomplexed ionic mineral from the source compound, are present in the formulation. Typically, such uncomplexed ionic mineral and/or ionic mineral source compounds are present in trace amounts. Alternatively, the formulations described herein may contain other uncomplexed compounds comprising ionic minerals, or other uncomplexed ionic minerals. Such compounds may be added to the formulation during processing, preferably following complex formation.

In one embodiment, at least one ionic mineral-ion exchange resin complex is combined with components selected from one or more of Vitamin C, Vitamin A, Vitamin D, Vitamin $B_3$, fluoride, folate, folic acid or a pharmaceutically salt thereof, sodium, potassium, calcium, omega-3-fatty acids, magnesium, chloride, phosphate, copper, fluoride, iodine, iron, selenium, zinc, boron, chromium, cobalt, germanium, gold, nickel, silver, iodine, molybdenum, platinum, sulfur, tin, and vanadium, amongst others.

For example, in one embodiment, a composition as described herein may contain iron in an amount from 0.1 mg to 1500 mg, 1 mg to 1000 mg, 5 mg to 100 mg, or about 10 to 50 mg, or about 15 to 20 mg/dosage unit. In another examples, suitable amounts of fluoride may be provided, e.g., by a compound such as sodium fluoride, sodium monofluorophosphate, or stannous fluoride. Examples of suitable amounts of the fluoride may range from 0.01 mg/day to 0.5 mg/day for infants to 1 to 3 mg/day for children and adults.

Omega-3 fatty acids are polyunsaturated fatty acids classified as essential because they cannot be synthesized in the body; they must be obtained from food. Important omega-3 fatty acids in human nutrition are: α-linolenic acid (ALA), eicosapentaenoic acid (EPA), arachidonic acid (ARA), and docosahexaenoic acid (DHA). Such omega-3 fatty acids are not assigned recommended daily intakes, but have acceptable daily intake amounts in the range of about 1.6 grams/day for men and about 1.1 grams/day for women.

In one embodiment, a pediatric unit dosage form comprises a ferrous-cation exchange resin complex (10 mg/iron), and further provides other components selected one or more of Vitamin A (palmitate) 1000-1700 International Units, preferably 1500 IU, Vitamin C (ascorbic acid) 20-50 mg, Vitamin $B_1$ 0.2 to 1, or about 0.4-0.8 mg, Vitamin $B_6$ (2 to 4 mg), Vitamin $B_3$ (3-5 mg, preferably 3.3 mg), Iron (ferric ammonium citrate) (2-10 mg, preferably 3.3 mg), Vitamin $D_3$ 100-500 i.u., Vitamin $E_5$-10 i.u., Vitamin $B_6$ (0.2 to 2 mg, or about 0.5 to 1 mg), Folic acid (50-1 mg, 50 mcg to 75 mcg, or about 65 mcg), Vitamin $B_{12}$ 1-2 mcg, Iodine 25 mcg, Magnesium (chloride) 4.2 mg, Zinc sulfate 3.3 mg, Copper sulfate 0.3 mg, Biotin 67 mcg, Vitamin $B_5$ (1-2 mg), Chlorine (chloride) 10 mg, Inositol (5-10 mg), Potassium (citrate) (5-10 mg), Manganese (sulfate) (0.5-1, preferably 0.8 mg), Vitamin $B_{10}$ (PABA) (0.25-0.5 mg, preferably 0.3 mg), Molybdenum (trioxide) 75-85 mcg), Vandadium (pentoxide) (75-95 mcg), Chromium (chloride) (30-35 mcg), and Selenium (sodium selenite) (30-35 mcg), fluoride, 0.25-0.5 mg. These amounts are typically delivered in a 1 mL dosage form and occasionally larger units.

In one embodiment, a liquid suspension containing a ferrous ion-cation resin complex as the active nutritional moiety or active pharmaceutical ingredient, termed interchangeably herein as the "API" is provided. In one embodiment, the ferrous resin complex is prepared from mixture of ferrous sulfate heptahydrate and the cation exchange resin (e.g., Amberlite IRP-69 resin, anhydrous) in the amount of 5-50% w/v, and preferably 15-25% w/v in the presence of an ascorbic acid antioxidant which is present in a suitable diluent (e.g., purified water) in an amount of 0.05% w/v to 5% w/v, preferably 0.05 to 0.2% w/v. A typical placebo base is composed of purified water (or other suitable diluent), anhydrous citric acid buffer (0.1 to 2% w/v, preferably 0.1 to 0.5% w/v), sweeteners including high fructose corn syrup (5-80% w/v, preferably 20-40% w/v) and sucralose (0.03 to 1.1% w/v, preferably 0.4 to 0.6% w/v), preservatives such as methylparaben (0.015-0.2% w/v, preferably 0.15-0.2% w/v) and propylparaben (0.01-1% w/v, preferably 0.01-0.02% w/v), a solubilizer such as glycerin (1-50% w/v, preferably 5-15% w/v), a suspending agents including starch instant clearjel (0.1-10% w/v, preferably 2-3% w/v) and xanthan gum (0.01-5% w/v, preferably 0.1-0.3% w/v), and flavoring (0.1-10% w/v, preferably 1-2% w/v). To form a liquid suspension formulation, the ferrous resin complex is added to the placebo suspension base, to which ascorbic acid in an amount of about 0.01-5% w/v, preferably, 0.01-0.5% w/v, and surfactant (e.g., Polysorbate 80) in an amount of 0.01-15% w/v, preferably about 0.1-0.5% w/v.

In another embodiment, a pediatric formulation contains a ferrous-cation exchange resin complex, Vitamin A, Vitamin C, and Vitamin D. Such a formulation may contain 10 mg iron, 1500 IU vitamin A, 35 mg Vitamin C, 400 IU Vitamin D. Such a formulation is desirably in the form of a liquid suspension containing polysorbate 80, citric acid, high fructose corn syrup, sucralose, glycerin, methylparaben, propylparaben, xanathan gum, starch instant cleargel, strawberry banana flavor, and water, optionally with dyes such as FD&C yellow #6 and FD&C #40. In one embodiment, this formulation is an alcohol and sugar-free liquid suspension which is delivered in a 2 mL daily dose. Optionally, the formulation further contains ferrous sulfate in trace amounts.

In another embodiment, a formulation provides a unit dosage form comprising an ionic mineral-ion exchange formulation in combination with one or more additional components selected from one ore more of the following. The amounts provided following the components are the presently recommended daily allowances (RDA) for vitamins, or recommended daily intakes, for certain adult populations unless otherwise noted. However, it will be readily understood that lower amounts may be selected for inclusion in a formulation an amount of 100% of the currently recommended Vitamin A (3500 IU (29% as Beta Carotene), Vitamin C (60 mg), Vitamin D (400 IU), Vitamin D (400 IU, Vitamin E (30 IU), Vitamin K 25 mcg (this provides 31% RDA), Thiamin 1.5 mg, Riboflavin, (1.7 mg), Niacin (20 mg), Vitamin B6 (2 mg), Folic Acid (400 mcg), Vitamin B 12 (6 mcg), Biotin (30 mcg), Pantothenic Acid (10 mg), Calcium (162 mg provides about 16% of the adult RDA), Iron (18 mg), Phosphorus (109 mg, 11% of RDA), Iodine (150 mcg), Magnesium (100 mg provides 25% of RDA), Zinc (15 mg), Selenium (20 mcg provides 29% of RDA), Copper (2 mg), Manganese (2 mg), Chromium (120 mcg), Molybdenum (75 mcg), Chloride (72 mg is 2% RDA), Potassium (80 mg is 2% of RDA). Optional components, for which no daily recommendation allowance is established include Boron 150 mcg, Nickel 5 mcg, Silicon 2 mg, Tin 10 mcg, Vandadium 10 mcg, Lutein 250 mcg, Lycopene 300 mcg.

In yet another aspect, a formulation adapted for use as a prenatal vitamin is provided. In one embodiment, a formulation contains an iron-cation exchange resin complex, in combination with a folic acid, folate, or other pharmaceutically acceptable salt thereof. Typically, such folic acid or salt thereof is present in an amount of about 50 mcg to about 1 mg), Such a formulation may further contain niacin or nicotinic acid (Vitamin $B_3$) and/or one or more additional nutrients.

In one embodiment, a dosage unit containing calcium is provided in a calcium-cation exchange mineral resin. Calcium may be provided in an amount of about 100 to about 1500 mg/dose. Typically, for infants, 210 mg/day is the RDA. For babies (7 to 12 months), 270 mg/day is the RDA. For children 1 to 3 years, the RDA is 500 mg/day; for 4 to 8 year olds, the RDA is 800 mg/day; for 9 to 13 year olds, the RDA is 1300 mg/day; for 14 to 18 year olds, the RDA is 1300 mg/day; for 19 to 50 year olds, the RDA is 1000 mg/day; for adults over 51, the RDA is 1200 mg/day. A dosage unit may be formulated such that one dosage unit provides the entire recommended daily allowance. Alternatively, it may be formulated to accommodate two or more dosage units being taken during the day.

Excipients other than those expressly described herein may be readily selected by one of skill in the art, taking into consideration the desired formulation. The formulations described herein can be prepared using the techniques described in this specification, and those which are well known to those of skill in the art.

Solid Formulations

In another aspect, an ionic mineral-ion exchange resin complex formulated as a tablet is provided. The tablet contains ionic mineral-ion exchange resin complex in an amount of about 10% w/w to about 90% w/w, more preferably 20% w/w to about 80% w/w, most preferably about 25% to about 35% w/w. In one embodiment, the tablet further contains bulking materials including mannitol in an amount of 5% w/w to 90% w/w, preferably 10% w/w to 15% w/w, and microcrystalline cellulose in an amount of 5% w/w to 90% w/w, preferably 10% w/w to 15% w/w, glidant such as silicon dioxide in an amount of 0.1% w/w to 5% w/w to 0.3% w/w to 0.8% w/w, and a disintegrant such as sodium starch glycolate in the amount of 0.2% w/w to 10% w/w.

In another aspect, an ionic mineral-ion exchange resin complex formulated as an orally disintegrating tablet is provided. The tablet contains ionic mineral-ion exchange resin complex in an amount of about 10% w/w to about 90% w/w, more preferably 20% w/w to about 80% w/w, most preferably about 25% to about 35% w/w. The tablet may also contain a disintegrating aid such as calcium silicate in the amount of 2% w/w to 80% w/w, preferably 6% w/w to 12% w/w, glidant such as silicon dioxide, in the amount of 0.1% w/w to 5% w/w, preferably 0.3% w/w to 0.8% w/w, superdisintegrant such as crospovidone in the amount of 0.5% w/w to 5% w/w, preferably 1% w/w to 2% w/w, bulking materials such as mannitol and microcrystalline cellulose in the amounts described for the tablets above, and a sweetener such as acesulfame potassium in the amount of 0.1% w/w to 5% w/w, preferably 0.2% w/w to 0.5% w/w.

In another aspect, tablets can be formed from the ionic mineral-ion exchange resin complex. Such tablets may include, e.g., a disintegrant and/or a disintegrating aid, and a glidant. In this context, disintegrants are components which facilitate rapid and consistent disintegration of the tablet in the patient's mouth. These components may be present in the formulation in an amount of from about 0.2% w/w to about 10% w/w, from about 0.5% w/w to about 5% w/w, from about 0.5% w/w to about 2% w/w, preferably about 1% w/w to about 2% w/w. Examples of suitable disintegrants include, e.g., sodium starch glycolate, crospovidone, croscarmellose sodium, low-substituted hydroxypropyl cellulose. A disintegrating aid, e.g., calcium silicate, may be present in the formulation in an amount of about 2% w/w to about 80% w/v, preferably about 5% w/w to about 15% w/w, and more preferably 6% w/w to 12% w/w.

A glidant may be present in an amount of about 0.1% w/w to about 5% w/w, and more preferably about 0.3% w/w to about 0.8% w/v. Examples of suitable glidants include, e.g., silicon dioxide including colloidal silicon dioxide, talc, stearic acid, or combinations thereof.

Still other excipients may be readily selected by one of skill in the art, taking into consideration the desired formulation. The formulations described herein can be prepared using the techniques described in this specification, and those which are well known to those of skill in the art.

Uses of the Compositions

In one aspect, a method of delivering an effective amount of an ionic mineral to a subject as a dietary supplement, therapeutic, or prophylactic agent is provided. The compositions described herein are particularly well suited for daily delivery. However, they may be delivered more (e.g., 2× or 3×/day), or less frequently (e.g., on alternate days, biweekly, weekly), as needed.

In another aspect, a formulation comprising a complex comprising a pharmaceutically effective amount of an ionic mineral component bound to a pharmaceutically acceptable ion exchange resin, and a pharmaceutically acceptable carrier. In one embodiment, the iron is delivered in amount sufficient to treat iron deficiency, including, e.g., iron deficiency anemia. The iron deficiency anemia may be, e.g., antepartum anemia or post-partum anemia. In one embodiment, a composition for adults contains non-toxic amounts in excess of the recommended daily allowances for iron provided above. Alternatively, a formulation providing the recommended daily dosage may be delivered, with the frequency of delivery adjusted depending upon the severity of the iron deficiency.

In another embodiment, a formulation comprising lithium-ion exchange resin complex can be used to treat mood disorders including, e.g., bi-polar disorder, mania, and depression. The suggested initial daily dosage for acute mania is 900 to 1800 mg (15 to 20 mg/kg), divided into 3 doses. Often, lithium treatment can be started at a dose between 600 and 900 mg/day, reaching a level of 1200 to 1800 mg in divided doses on the second day. Elderly and debilitated patients, and those with significant renal impairment should be prescribed lithium with particular caution. Starting dose should not exceed 300 mg/day accompanied by frequent serum level monitoring. Serum concentrations of 0.4 to 0.6 mmol/L are usually effective in elderly patients. In children, 0.5 to 1.5 $g/m^2$ in divided doses for the acute phase; the maintenance dose should be adjusted to maintain lithium serum concentrations of 0.5 to 1.2 mmol/L.

Products

In another aspect, a product containing an ionic mineral-ion exchange resin complex is provided.

In some embodiments, the ionic mineral-ion exchange resin complexes of the invention are in packs in a form ready for administration, e.g., a blister pack, a bottle, syringes, foil packs, pouches, or other suitable container. In other embodiments, the compositions described herein are in concentrated form in packs, optionally with the diluent required to make a final suspension for administration. In still other embodiments, the product contains a compound in solid form and, optionally, a separate container with a suitable suspension base or other carrier for the ionic mineral-ion exchange resin complex.

In still other embodiments, the above packs/kits include other components, e.g., a meter dose apparatus/device, instructions for dilution, mixing and/or administration of the product, other containers, nasogastric tubes, etc. Other such pack/kit components will be readily apparent to one of ordinary skill in the art.

Devices have been described, and many are commercially available, which provide for metered administration, including a metered syringe or dispenser cup, and/or metered-dose inhalers. For example, various liquid metering devices for squeezable bottles have been described [U.S. Pat. No. 6,997, 358, U.S. Pat. No. 3,146,919, filed in 1960, U.S. Pat. No. 3,567,079, filed in 1968, and in GB 2201395, filed in 1986.] A device for dispensing multiple compositions is provided in U.S. Pat. No. 6,997,219.

Methods and apparatus for delivery of compositions through nasogastric tubes are well known to those of ordinary skill in the art. See, e.g., E. Bryson, "Drug Administration via Nasogastric Tube", *Nurs Times*, Apr. 19-25, 2001, 97(16):51. The compositions described herein can be readily delivered using such devices. Suitable nasogastric tubes are available commercially and/or have been described. See, e.g., U.S. Pat. No. 5,334,166; U.S. Pat. No. 5,322,073; U.S. Pat. No. 4,619,673; U.S. Pat. No. 4,363,323.

EXAMPLES

The following examples are provided to more specifically illustrate the compositions and are not intended to be limiting. They are for illustrative purposes only and it is realized that changes and variations can be made without departing from the spirit and scope of the invention.

Example 1 illustrates a liquid suspension comprising an ionic mineral-cationic exchange resin complex with the following illustrative excipients:

Example 2 illustrates a formulation of the invention containing vitamins in combination with an ionic mineral-ion exchange resin complex.

Example 3 illustrates a tablet containing a charged mineral-ionic exchange resin complex of the invention using the following illustrative excipients.

Example 4 illustrates an orally disintegrating tablet containing a charged mineral-ionic exchange resin complex of the invention in a formulation having the following illustrative excipients.

Examples

Example 1

Suspension

Formula

| Ingredient | Quantity |
| --- | --- |
| Ferrous Resin Complex | |
| Ferrous Sulfate Heptahydrate | 40.91 g |
| Ascorbic Acid | 1 g |
| Purified Water | 1 L |
| Amberlite IRP-69 Resin (anhydrous) | 107 g |
| Placebo Suspension Base | |
| Purified Water | 1,000 g |
| Citric Acid, anhydrous | 8 g |
| FD&C Yellow #6 | 0.064 g |
| FD&C Red #40 | 0.144 g |
| High Fructose Corn Syrup 42 | 1,200 g |
| Methylparaben | 7.2 g |
| Propylparaben | 0.8 g |
| Glycerin | 400 g |
| Sucralose | 20 g |
| Starch Instant Clearjel | 100.26 g |
| Xanthan Gum | 8.7 g |
| Strawberry/Banana flavor | 44.88 g |
| Purified Water | QS 3,484 g |
| Ferrous Suspension | |
| Purified Water | 50 g |
| Ascorbic Acid | 0.5 g |
| Polysorbate 80 | 0.55 g |
| Ferrous Resin Complex | 76.93 g |
| Placebo Suspension base | 435.6 g |
| Purified Water | QS 500 mL |

Process

The ferrous resin complex of this example, Example 1, was prepared by first dissolving 1 g of ascorbic acid in 1 L of Purified Water, followed by the addition of 40.91 g of Ferrous Sulfate Heptahydrate with continued mixing until dissolved. The Amberlite IRP-69 Resin of 107 g was then added to the solution and mixed for 4 hours. Upon completion, the slurry was transferred to a laboratory filtration apparatus (Pall ESF 60) equipped with 10 μm stainless steel screen and filtered under pressure. The residue was further rinsed and filtered with sufficient amount of Purified Water three times. The wet ferrous resin complex was used for preparing the final suspension.

Placebo suspension base was prepared by dissolving 8 g of citric acid in 1,000 g of purified water in the main container, followed by adding 1,200 g of high fructose corn syrup. Sucralose (Splenda™) of 20 g was then added to the main container and mixed until dissolved. FD&C Yellow #6, and FD&C Red #40 were added to the main container and mixed until dissolved. In a separate container, 400 g of glycerin was added and heated to 45-50° C. before additions of 7.2 g of methylparaben and 0.8 g of propylparaben. After both parabens were dissolved, the solution was cooled to room temperature and 8.7 g of Xanthan gum was uniformly dispersed in it to form the gum dispersion. In the main container, 100.26 g of starch instant clearjel was slowly added with the aid of high speed mixing (Silverson mixer) until uniform. The gum dispersion was then slowly added to the main container and mixed well. The flavor of 44.88 g was then added and QS to 3,484 g with purified water.

The final suspension was prepared by dissolving 0.5 g of ascorbic acid and 0.55 g of polysorbate 80 in 50 g of purified water, followed by the addition of placebo suspension base, mixed until uniform. The wet ferrous resin complex was then slowly introduced to the above solution under continuous mixing to achieve uniformity. Purified water was last added to adjust the volume to 500 mL and mixed for 15-30 minutes. The final suspension was packaged in 4 oz PET bottles for further stability evaluations.

Example 2

Suspension

This example provides a process which eliminates the need for isolation of the Ferrous Resin Complex and which permits all ingredients to be added and processed in the same container. By forming the complex in situ, this process enhances the efficiency of total process time and increases the yield due to consolidated processing steps.

Formula

| Ingredient | Quantity |
| --- | --- |
| Purified Water | |
| Citric Acid Anhydrous | 1 g |
| Ascorbic Acid | 30 g |
| Sodium Fluoride | 0.079 g |
| Ferrous Sulfate Heptahydrate | 12.45 g |
| Amberlite IRP-60 Resin | 37.34 g |
| High Fructose Corn Syrup 42 | 150 g |
| Sucralose | 2.5 g |
| FD&C Yellow #6 | 0.008 g |
| FD&C Red #40 | 0.018 g |
| Glycerin | 50 g |
| Methylparaben | 0.9 g |
| Propylparaben | 0.1 g |
| Polysorbate 80 | 0.55 g |

-continued

| Ingredient | Quantity |
| --- | --- |
| Vitamin D | 5 mg |
| Vitamin A | 0.42 g |
| Xanthan Gum | 1.09 g |
| Starch Instant Clearjel | 12.54 g |
| Strawberry/Banana flavor | 5.61 g |
| Purified Water | QS 500 mL |

Process

The suspension was prepared by first dissolving 1 g of citric acid, 30 g of ascorbic acid and 0.079 g of sodium fluoride in 125 g of Purified Water in the main container, followed by the addition of 12.45 g of Ferrous Sulfate Heptahydrate with continued mixing until dissolved. The Amberlite IRP-69 Resin of 37.34 g was then added to the solution and mixed for 1 hour. In a separate container, 50 g of Glycerin is heated to 50° C. before addition of 0.9 of Methylparaben and 0.1 g of Propylparaben and mixed until dissolved. The solution was cooled to room temperature, added 0.55 g of Polysorbate 80 and mixed to dissolved (Glycerin Solution). Vitamin D of 5 mg was then added to the Glycerin solution, mixed until dissolved followed by 0.42 g of Vitamin A was slowly dispersed with continuous mixing. The Xanthan Gum of 1.09 g was then dispersed into the solution (Gum dispersion). In the main container, High Fructose Corn syrup of 150 g and Sucralose of 2.5 g were added and mixed to dissolve. The FD&C Yellow #6 of 0.008 g and FD&C Red #40 of 0.018 g were then added to the main container with continuous mixing until dissolved. Slowly dispersed 12.54 g of Starch instant Clearjel in the main container using high shear mixer (Silverson) followed by adding the Gum Slurry. Upon completion, the product was transferred to a gentle mixer (VWR) and added 5.61 g Strawberry/Banana Flavor and mixed until uniform. The final volume was adjusted to 500 mL with Purified Water and mixed for an additional 20-30 minutes. The final suspension was packaged in 4 oz PET bottles for further stability evaluations.

Example 3

Immediate Release Tablets

Formula

| Ingredient | Quantity |
| --- | --- |
| Ferrous Resin Complex | |
| Ferrous Sulfate Heptahydrate | 204.55 g |
| Ascorbic Acid | 5 g |
| Purified Water | 5 L |
| Amberlite IRP-69 Resin | 535 g |
| Ferrous IR Tablets | |
| Ferrous Resin Complex | 78.47 g |
| Mannitol | 66.67 g |
| Microcrystalline Cellulose | 66.67 g |
| Silicon Dioxide | 3.33 g |
| Sodium Starch Glycolate | 5 g |

Process

The ferrous resin complex was prepared by first dissolving 5 g of ascorbic acid in 5 L of Purified Water, followed by the addition of 204.55 g of Ferrous Sulfate Heptahydrate with continued mixing until dissolved. The Amberlite IRP-69 Resin of 535 g was then added to the solution and mixed for 4 hours. Upon completion, the slurry was transferred to a laboratory filtration apparatus (Pall ESF 60) equipped with 10 µm stainless steel screen and filtered under pressure. The residue was further rinsed and filtered with sufficient amount of Purified Water three times. The wet ferrous resin complex was then dried under ambient condition until the moisture level suitable for tableting.

The powder blend was prepared by adding 78.47 g Ferrous Resin Complex, 66.67 g Mannitol, 66.67 g Microcrystalline Cellulose, 3.33 g Silicon Dioxide and 5 g Sodium Starch Glycolate to a cube blender (Erweka) and mix for 5 minutes. The powder blend was then removed from the cube blender and passed through 25 mesh screen, transferred back to the cube blender and mixed for an additional 3 minutes. The tablets were prepared by transferring the final blend to a tablet press (GlobePharm Mini-Press II) equipped with ⅜" standard concave tooling and compressed into tablets with a target weight of 472.4 mg and hardness of 5-7 Kp.

Example 4

Orally Disintegrating Tablet—Immediate Release Tablets

Formula

| Ingredient | Quantity |
| --- | --- |
| Ferrous Resin Complex (from example 3) | |
| Ferrous Sulfate Heptahydrate | 40.91 g |
| Ascorbic Acid | 1 g |
| Purified Water | 1 L |
| Amberlite IRP-69 Resin (anhydrous) | 107 g |
| Ferrous ODT IR Tablets | |
| Ferrous Resin Complex | 78.47 g |
| Calcium Silicate | 46 g |
| Silicon Dioxide | 3.33 g |
| Mannitol | 80 g |
| Microcrystalline Cellulose | 66.7 g |
| Crospovidone | 6.67 g |
| Acesulfame Potassium | 1.67 g |

Process

The ferrous resin complex was prepared as shown in example 3. The powder blend was prepared by adding 78.47 g Ferrous Resin Complex, 46 g Calcium Silicate, 3.33 g Silicon Dioxide, 80 g Mannitol, 66.67 g Microcrystalline Cellulose, 6.67 g Crospovidone and 1.67 g Acesulfame Potassium to a cube blender (Erweka) and mix for 5 minutes. The powder blend was then removed from the cube blender and passed through 25 mesh screen, transferred back to the cube blender and mixed for an additional 3 minutes. The tablets were prepared by transferring the final blend to a tablet press (GlobePharm Mini-Press II) equipped with ½" standard concave tooling and compressed into tablets with a target weight of 848.4 mg and hardness of 4-5 Kp.

All patents, patent publications, and other publications listed in this specification are incorporated herein by reference. While the invention has been described with reference to a particularly preferred embodiment, it will be appreciated that modifications can be made without departing from the spirit of the invention. Such modifications are intended to fall within the scope of the appended claims.

The invention claimed is:

1. A process for preparing an orally ingestible aqueous iron suspension in situ comprising:
   combining a pharmaceutically acceptable cation exchange resin with an aqueous solution comprising an antioxidant and a ferrous iron to form an aqueous suspension;
   stirring the aqueous suspension for a sufficient amount of time to permit formation of a ferrous-ion exchange resin complex comprising about 25% to about 70% by weight ferrous iron based on the weight of the ferrous-ion exchange resin complex;
   optionally combining one or more additional active components with said aqueous suspension prior to completion of complex formation; and
   mixing said aqueous suspension comprising the ferrous-ion exchange resin complex with one or more active or inactive components to form the orally ingestible ferrous aqueous suspension, wherein the process is performed in a single container without the need for isolation or drying of the mineral-ion exchange resin complex prior to forming the orally ingestible liquid suspension.

2. The process according to claim 1, wherein the antioxidant is present in an amount of about 2.5% w/v to about 10% w/v.

3. The process according to claim 1, wherein ferrous iron combined into the aqueous solution is added in the form of ferrous sulfate or a hydrate thereof.

4. The process according to claim 1, wherein the ferrous iron is ferrous sulfate heptahydrate.

5. The process according to claim 1, wherein the antioxidant is selected from one or more of ascorbic acid and pharmaceutically acceptable salts thereof, butylated hydroxyanisole, butylated hydroxytoluene, sodium metabisulfite, and sodium bisulfate.

6. The process according to claim 1, wherein the orally ingestible ferrous aqueous suspension comprises the ferrous-ion exchange resin complex and butylated hydroxyanisole.

7. The process according to claim 6, wherein the orally ingestible ferrous aqueous suspension further comprises Vitamin C.

8. The process according to claim 6, wherein the orally ingestible ferrous aqueous suspension further comprises Vitamin A and Vitamin D.

9. The process according to claim 6, wherein the orally ingestible ferrous aqueous suspension further comprises fluoride.

10. The process according to claim 1, wherein the antioxidant is present in an amount of about 0.05 to about 2% w/v.

11. The process according to claim 1, wherein the ferrous iron component is mixed with the ion exchange resin in an amount to allow loading of about 25 to about 40% by weight, of the ferrous iron onto the ion exchange resin.

12. The process according to claim 1, wherein the cation exchange resin has an average particle size of about 5 microns to about 150 microns.

13. The process according to claim 1, wherein the iron is a ferrous sulfate and the orally ingestible aqueous iron suspension comprising the iron-cation exchange complex further contains ferrous sulfate.

14. The process according to claim 1, wherein the complex is in an amount of about 5 to about 50% w/v in the aqueous suspension.

15. The process according to claim 1, wherein the complex is in an amount of about 10 to about 25% w/v in the aqueous suspension.

16. The process according to claim 1, wherein the ferrous iron is provided from a salt or complex selected from the group consisting of ferrous sulfate, ferrous fumarate, ferrous polymaltose, ferrous bisglycinate, ferrous glycine sulphate, ferrous gluconate, ferrous citrate, ferrous carbonate, ferrous lactate, ferrous succinate, ferrous ascorbate, an amino acid ferrous complex, or a hydrate thereof.

17. The process according to claim 1, wherein ferrous iron is added into a solution in the form of a salt or complex, which salt or complex is dissolved in an aqueous solution prior to reacting with the ion exchange resin complex.

18. The process according to claim 1, wherein the liquid suspension further comprises an omega-3-fatty acid component and/or folate.

19. The process according to claim 1, wherein an antioxidant and/or a fluoride compound are added prior to the reaction between the at least one ionic mineral and the ion exchange resin.

20. The process according to claim 1, wherein one or more vitamins or minerals are added after forming the ferrous iron-ion exchange resin complex.

21. The process according to claim 19, wherein the fluoride compound or complex is selected from the group consisting of sodium fluoride, sodium monofluorophosphate, and stannous fluoride.

22. The process according to claim 20, wherein the vitamin is selected from the group consisting of one or more of Vitamin A, Vitamin C and Vitamin D.

23. The process according to claim 20, wherein the one or more vitamins or nutrients is selected from the group consisting of one or more of Vitamin A, niacin, nicotinic aid, folate, folic acid, Vitamin C, Vitamin D, Vitamin K, Vitamin E, and the Vitamin B family, and fluoride.

24. A process for preparing an orally ingestible aqueous liquid iron suspension in a single vessel comprising:
   mixing an aqueous suspension in a single vessel, said aqueous suspension comprising a pharmaceutically acceptable cation exchange resin, an antioxidant, water and a ferrous iron for a sufficient amount of time to permit formation of a ferrous-cation exchange resin complex comprising about 25% to about 70% by weight ferrous iron based on the weight of the ferrous-ion exchange resin complex;
   adding one or more active or inactive components into the single vessel containing the aqueous liquid suspension to form the orally ingestible iron aqueous suspension, wherein the process is performed without isolation or drying of the iron-cation exchange resin complex prior to forming the orally ingestible liquid suspension.

* * * * *